Figure 1:
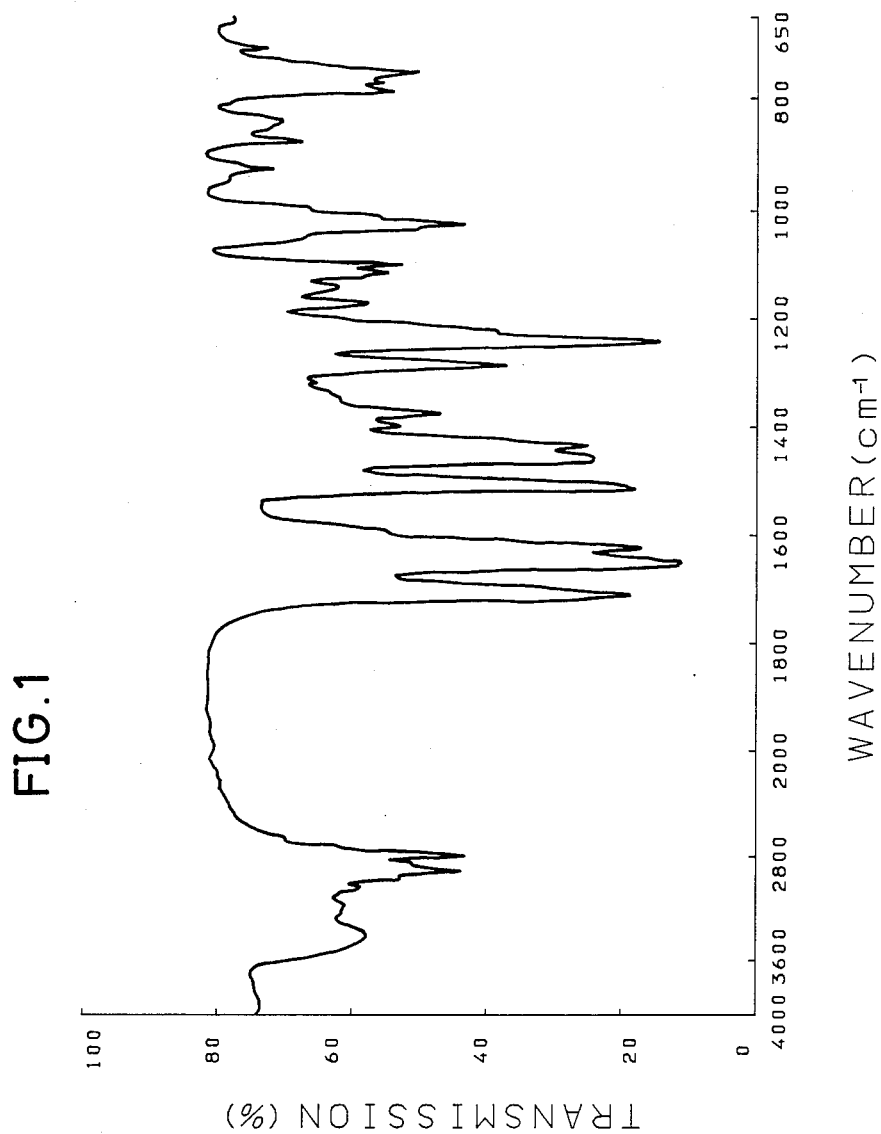

United States Patent [19]

Fukami et al.

[11] Patent Number: 4,716,161
[45] Date of Patent: Dec. 29, 1987

[54] PHENYLPIPERAZINE DERIVATIVES AND THEIR ACID ADDITION SALTS

[75] Inventors: Harukazu Fukami, Kyoto; Ryoji Kikumoto, Machida; Kenichiro Nakao, Tokyo; Issei Nitta, Machida; Shinya Inoue, Yokohama, all of Japan

[73] Assignee: Mitsubishi Chemical Industries Limited, Tokyo, Japan

[21] Appl. No.: 719,456

[22] Filed: Apr. 3, 1985

[30] Foreign Application Priority Data

| Apr. 17, 1984 [JP] | Japan | 59-77006 |
| Sep. 28, 1984 [JP] | Japan | 59-203743 |
| Oct. 5, 1984 [JP] | Japan | 59-209133 |
| Jan. 8, 1985 [JP] | Japan | 60-1246 |

[51] Int. Cl.$^4$ .................... A61K 31/54; C07D 417/06
[52] U.S. Cl. ................................. 514/222; 514/253; 544/9; 544/12; 544/13; 544/251; 544/285
[58] Field of Search ............... 544/285, 251, 9, 12, 544/13; 514/253, 222

[56] References Cited

U.S. PATENT DOCUMENTS

| 3,267,096 | 8/1966 | Hayao et al. | 544/12 |
| 3,983,120 | 9/1976 | Beverung et al. | 544/286 |

FOREIGN PATENT DOCUMENTS

580084 9/1976 Fed. Rep. of Germany.

OTHER PUBLICATIONS

Brown, *Fused Pyrimidines-Quinazolines*, Part 1, 1967, Interscience Publishers, N.Y., pp. 69–80.
Nagano, et al., "Chemical Abstracts", vol. 100, 1984, col. 100:6547p.
Ishikawa, "Chemical Abstracts", vol. 101, 1984, col. 101:17967x.
"Chemical Abstracts", vol. 102, 1985, col. 102:132073k.
Uchida, et al., "Chemical Abstracts", vol. 103, 1985 col. 103:64598d.

Primary Examiner—Glennon H. Hollrah
Assistant Examiner—James H. Turnipseed
Attorney, Agent, or Firm—Oblon, Fisher, Spivak, McClelland, & Maier

[57] ABSTRACT

A phenylpiperazine derivative according to the present invention has the following general formula [I]:

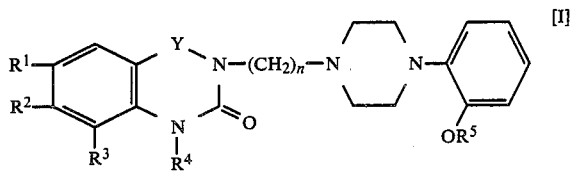

wherein
$R^1$, $R^2$ and $R^3$ are independently hydrogen or alkoxy group having 1 to 3 carbon atoms, or
$R^1$ and $R^2$ or $R^2$ and $R^3$ together with carbon atoms to which they are attached form —O(CH$_2$)$_m$O— wherein m is an integer of 1 to 3, or
either $R^1$ or $R^2$ is amine residue selected from the group consisting of —NH$_2$, —NHSO$_2$CH$_3$, —NHCOCH$_3$ and —NHCONH$_2$ and the other is hydrogen or alkoxy group of 1 to 3 carbon atoms and $R^3$ is hydrogen;
$R^4$ and $R^5$ are independently hydrogen or alkyl group of 1 to 3 carbon atoms;
Y is —CO— or —SO$_2$— provided that at least one of $R^1$ and $R^2$ is not hydrogen when Y is —CO—; and
n is an integer of 2 to 4.

An acid addition salt of the phenylpiperazine derivative having the general formula [I] is included in the present invention. The phenylpiperazine derivative as well as its acid addition salt according to the present invention have the ability to reduce the blood pressure.

16 Claims, 13 Drawing Figures

PHENYLPIPERAZINE DERIVATIVES AND THEIR ACID ADDITION SALTS

The present invention relates to phenylpiperazine derivatives and acid addition salts thereof having an ability to reduce the blood pressure.

In particular, the present invention relates to compounds of the general formula [I]:

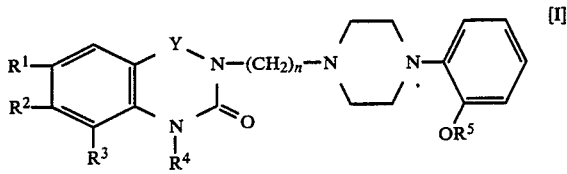

wherein
$R^1$, $R^2$ and $R^3$ are independently hydrogen or alkoxy group having 1 to 3 carbon atoms, or
$R^1$ and $R^2$ or $R^2$ and $R^3$ together with carbon atoms to which they are attached form $-O(CH_2)_mO-$ wherein m is an integer of 1 to 3, or
either $R^1$ or $R^2$ is amine residue selected from the group consisting of $-NH_2$, $-NHSO_2CH_3-$, $-NHCOCH_3$ and $-NHCONH_2$ and the other is hydrogen or alkoxy group having 1 to 3 carbon atoms and $R^3$ is hydrogen;
$R^4$ and $R^5$ are independently hydrogen or alkyl group having 1 to 3 carbon atoms;
Y is $-CO-$ or $-SO_2-$ provided that at least one of $R^1$ and $R^2$ is not hydrogen when Y is $-CO-$; and
n is an integer of 2 to 4,
and their acid addition salts.

Typical and non-limitative examples of the compounds of the general formula [I] according to the present invention (hereinafter referred to as "the present compound") are as follows.

3-[2-[4-(2-methoxyphenyl)-1-piperazinyl]ethyl]-6,7-dimethoxy-1,2,3,4-tetrahydroquinazoline-2,4-dione,
3-[2-[4-(2-methoxyphenyl)-1-piperazinyl]ethyl]-6,7-diethoxy-1,2,3,4-tetrahydroquinazoline-2,4-dione,
3-[2-[4-(2-methoxyphenyl)-1-piperazinyl]ethyl]-6,7-dipropoxy-1,2,3,4-tetrahydroquinazoline-2,4-dione,
3-[2-[4-(2-methoxyphenyl)-1-piperazinyl]ethyl]-6,7-diisopropoxy-1,2,3,4-tetrahydroquinazoline-2,4-dione,
3-[2-[4-(2-methoxyphenyl)-1-piperazinyl]ethyl]-6,7-methylenedioxy-1,2,3,4-tetrahydroquinazoline-2,4-dione,
3-[2-[4-(2-methoxyphenyl)-1-piperazinyl]ethyl]-6,7-dimethylenedioxy-1,2,3,4-tetrahydroquinazoline-2,4-dione,
3-[2-[4-(2-methoxyphenyl)-1-piperazinyl]ethyl]-6,7-trimethylenedioxy-1,2,3,4-tetrahydroquinazoline-2,4-dione,
3-[2-[4-(2-methoxyphenyl)-1-piperazinyl]ethyl]-7-amino-1,2,3,4-tetrahydroquinazoline-2,4-dione,
3-[2-[4-(2-methoxyphenyl)-1-piperazinyl]ethyl]-7-amino-6-methoxy-1,2,3,4-tetrahydroquinazoline-2,4-dione,
3-[2-[4-(2-methoxyphenyl)-1-piperazinyl]ethyl]-7-amino-6-ethoxy-1,2,3,4-tetrahydroquinazoline-2,4-dione,
3-[2-[4-(2-methoxyphenyl)-1-piperazinyl]ethyl]-7-amino-6-propoxy-1,2,3,4-tetrahydroquinazoline-2,4-dione,
3-[2-[4-(2-methoxyphenyl)-1-piperazinyl]ethyl]-7-amino-6-isopropoxy-1,2,3,4-tetrahydroquinazoline-2,4-dione,
3-[2-[4-(2-methoxyphenyl)-1-piperazinyl]ethyl]-7-methanesulfonylamino-1,2,3,4-tetrahydroquinazoline-2,4-dione,
3-[2-[4-(2-methoxyphenyl)-1-piperazinyl]ethyl]-7-methanesulfonylamino-6-methoxy-1,2,3,4-tetrahydroquinazoline-2,4-dione,
3-[2-[4-(2-methoxyphenyl)-1-piperazinyl]ethyl]-7-methanesulfonylamino-6-ethoxy-1,2,3,4-tetrahydroquinazoline-2,4-dione,
3-[2-[4-(2-methoxyphenyl)-1-piperazinyl]ethyl]-7-methanesulfonylamino-6-propoxy-1,2,3,4-tetrahydroquinazoline-2,4-dione,
3-[2-[4-(2-methoxyphenyl)-1-piperazinyl]ethyl]-7-methanesulfonylamino-6-isopropoxy-1,2,3,4-tetrahydroquinazoline-2,4-dione,
3-[2-[4-(2-methoxyphenyl)-1-piperazinyl]ethyl]-7-acetylamino-1,2,3,4-tetrahydroquinazoline-2,4-dione,
3-[2-[4-(2-methoxyphenyl)-1-piperazinyl]ethyl]-7-acetylamino-6-methoxy-1,2,3,4-tetrahydroquinazoline-2,4-dione,
3-[2-[4-(2-methoxyphenyl)-1-piperazinyl]ethyl]-7-acetylamino-6-ethoxy-1,2,3,4-tetrahydroquinazoline-2,4-dione,
3-[2-[4-(2-methoxyphenyl)-1-piperazinyl]ethyl]-7-acetylamino-6-propoxy-1,2,3,4-tetrahydroquinazoline-2,4-dione,
3-[2-[4-(2-methoxyphenyl)-1-piperazinyl]ethyl]-7-acetylamino-6-isopropoxy-1,2,3,4-tetrahydroquinazoline-2,4-dione,
3-[2-[4-(2-methoxyphenyl)-1-piperazinyl]ethyl]-7-carbamoylamino-1,2,3,4-tetrahydroquinazoline-2,4-dione,
3-[2-[4-(2-methoxyphenyl)-1-piperazinyl]ethyl]-7-carbamoylamino-6-methoxy-1,2,3,4-tetrahydroquinazoline-2,4-dione,
3-[2-[4-(2-methoxyphenyl)-1-piperazinyl]ethyl]-7-carbamoylamino-6-ethoxy-1,2,3,4-tetrahydroquinazoline-2,4-dione,
3-[2-[4-(2-methoxyphenyl)-1-piperazinyl]ethyl]-7-carbamoylamino-6-propoxy-1,2,3,4-tetrahydroquinazoline-2,4-dione,
3-[2-[4-(2-methoxyphenyl)-1-piperazinyl]ethyl]-7-carbamoylamino-6-isopropoxy-1,2,3,4-tetrahydroquinazoline-2,4-dione,
3-[2-[4-(2-methoxyphenyl)-1-piperazinyl]ethyl]-6-amino-1,2,3,4-tetrahydroquinazoline-2,4-dione,
3-[2-[4-(2-methoxyphenyl)-1-piperazinyl]ethyl]-6-amino-7-methoxy-1,2,3,4-tetrahydroquinazoline-2,4-dione,
3-[2-[4-(2-methoxyphenyl)-1-piperazinyl]ethyl]-6-amino-7-ethoxy-1,2,3,4-tetrahydroquinazoline-2,4-dione,
3-[2-[4-(2-methoxyphenyl)-1-piperazinyl]ethyl]-6-amino-7-propoxy-1,2,3,4-tetrahydroquinazoline-2,4-dione,
3-[2-[4-(2-methoxyphenyl)-1-piperazinyl]ethyl]-6-amino-7-isopropoxy-1,2,3,4-tetrahydroquinazoline-2,4-dione,
3-[2-[4-(2-methoxyphenyl)-1-piperazinyl]ethyl]-6-methanesulfonylamino-1,2,3,4-tetrahydroquinazoline-2,4-dione,
3-[2-[4-(2-methoxyphenyl)-1-piperazinyl]ethyl]-6-methanesulfonylamino-7-methoxy-1,2,3,4-tetrahydroquinazoline-2,4-dione, 3-[2-[4-(2-methoxyphenyl)-1-piperazinyl]ethyl]-6-methanesulfonylamino-7-ethoxy-1,2,3,4-tetrahydroquinazoline-2,4-dione,
3-[2-[4-(2-methoxyphenyl)-1-piperazinyl]ethyl]-6-methanesulfonylamino-7-propoxy-1,2,3,4-tetrahydroquinazoline-2,4-dione,
3-[2-[4-(2-methoxyphenyl)-1-piperazinyl]ethyl]-6-methanesulfonylamino-7-isopropoxy-1,2,3,4-tetrahydroquinazoline-2,4-dione,
3-[2-[4-(2-methoxyphenyl)-1-piperazinyl]ethyl]-6-acetylamino-1,2,3,4-tetrahydroquinazoline-2,4-dione,
3-[2-[4-(2-methoxyphenyl)-1-piperazinyl]ethyl]-6-acetylamino-7-methoxy-1,2,3,4-tetrahydroquinazoline-2,4-dione,
3-[2-[4-(2-methoxyphenyl)-1-piperazinyl]ethyl]-6-acetylamino-7-ethoxy-1,2,3,4-tetrahydroquinazoline-2,4-dione,
3-[2-[4-(2-methoxyphenyl)-1-piperazinyl]ethyl]-6-acetylamino-7-propoxy-1,2,3,4-tetrahydroquinazoline-2,4-dione,
3-[2-[4-(2-methoxyphenyl)-1-piperazinyl]ethyl]-6-acetylamino-7-isopropoxy-1,2,3,4-tetrahydroquinazoline-2,4-dione,
3-[2-[4-(2-methoxyphenyl)-1-piperazinyl]ethyl]-6-carbamoylamino-1,2,3,4-tetrahydroquinazoline-2,4-dione,
3-[2-[4-(2-methoxyphenyl)-1-piperazinyl]ethyl]-6-carbamoylamino-7-methoxy-1,2,3,4-tetrahydroquinazoline-2,4-dione,
3-[2-[4-(2-methoxyphenyl)-1-piperazinyl]ethyl]-6-carbamoylamino-7-ethoxy-1,2,3,4-tetrahydroquinazoline-2,4-dione,
3-[2-[4-(2-methoxyphenyl)-1-piperazinyl]ethyl]-6-carbamoylamino-7-propoxy-1,2,3,4-tetrahydroquinazoline-2,4-dione,
3-[2-[4-(2-methoxyphenyl)-1-piperazinyl]ethyl]-6-carbamoylamino-7-isopropoxy-1,2,3,4-tetrahydroquinazoline-2,4-dione,
3-[2-[4-(2-methoxyphenyl)-1-piperazinyl]ethyl]-6-methoxy-1,2,3,4-tetrahydroquinazoline-2,4-dione,
3-[2-[4-(2-methoxyphenyl)-1-piperazinyl]ethyl]-6-ethoxy-1,2,3,4-tetrahydroquinazoline-2,4-dione,
3-[2-[4-(2-methoxyphenyl)-1-piperazinyl]ethyl]-6-propoxy-1,2,3,4-tetrahydroquinazoline-2,4-dione,
3-[2-[4-(2-methoxyphenyl)-1-piperazinyl]ethyl]-6-isopropoxy-1,2,3,4-tetrahydroquinazoline-2,4-dione,
3-[2-[4-(2-methoxyphenyl)-1-piperazinyl]ethyl]-7-methoxy-1,2,3,4-tetrahydroquinazoline-2,4-dione,
3-[2-[4-(2-methoxyphenyl)-1-piperazinyl]ethyl]-7-ethoxy-1,2,3,4-tetrahydroquinazoline-2,4-dione,
3-[2-[4-(2-methoxyphenyl)-1-piperazinyl]ethyl]-7-propoxy-1,2,3,4-tetrahydroquinazoline-2,4-dione, and
3-[2-[4-(2-methoxyphenyl)-1-piperazinyl]ethyl]-7-isopropoxy-1,2,3,4-tetrahydroquinazoline-2,4-dione.

The compounds illustrated above have the general formula [I] wherein $R^3$ and $R^4$ are hydrogen atoms, $R^5$ is methyl, Y is —CO— and n is 2, but the compounds having the general formula [I] wherein $R^3$ is alkoxy having 1 to 3 carbon atoms, $R^4$ is alkyl having 1 to 3 carbon atoms, $R^5$ is hydrogen or alkyl other than methyl, Y is —CO— and n is 3 or 4 and the others are as herein defined, for example, 3-[3-[4-(2-methoxyphenyl)-1-piperazinyl]propyl]-6,7-dimethoxy-1,2,3,4-tetrahydroquinazoline-2,4-dione,
3-[3-[4-(2-methoxyphenyl)-1-piperazinyl]propyl]-6,7-methylenedioxy-1,2,3,4-tetrahydroquinazoline-2,4-dione,
3-[3-[4-(2-methoxyphenyl)-1-piperazinyl]propyl]-6,7-dimethylenedioxy-1,2,3,4-tetrahydroquinazoline-2,4-dione,
3-[3-[4-(2-methoxyphenyl)-1-piperazinyl]propyl]-6,7-trimethylenedioxy-1,2,3,4-tetrahydroquinazoline-2,4-dione,
3-[4-[4-(2-methoxyphenyl)-1-piperazinyl]butyl]-6,7-trimethylenedioxy-1,2,3,4-tetrahydroquinazoline-2,4-dione,
3-[2-[4-(2-methoxyphenyl)-1-piperazinyl]ethyl]-6,7-dimethoxy-1-methyl-1,2,3,4-tetrahydroquinazoline-2,4-dione,
3-[2-[4-(2-methoxyphenyl)-1-piperazinyl]ethyl]-6,7-methylenedioxy-1-methyl-1,2,3,4-tetrahydroquinazoline-2,4-dione,
3-[2-[4-(2-methoxyphenyl)-1-piperazinyl]ethyl]-6,7-dimethylenedioxy-1-methyl-1,2,3,4-tetrahydroquinazoline-2,4-dione,
3-[2-[4-(2-methoxyphenyl)-1-piperazinyl]ethyl]-6,7-trimethylenedioxy-1-methyl-1,2,3,4-tetrahydroquinazoline-2,4-dione,
3-[2-[4-(2-methoxyphenyl)-1-piperazinyl]ethyl]-6,7-trimethylenedioxy-1-ethyl-1,2,3,4-tetrahydroquinazoline-2,4-dione, and
3-[2-[4-(2-methoxyphenyl)-1-piperazinyl]ethyl]-6,7-trimethylenedioxy-1-propyl-1,2,3,4-tetrahydroquinazoline-2,4-dione,
are, of course, included in the scope of the present compounds.

And, the following compounds having the general formula [I] wherein Y is —$SO_2$— and the others are as herein defined can be exemplified, without limitation.

2-[2-[4-(2-methoxyphenyl)-1-piperazinyl]ethyl]-3,4-dihydro-1,2,4-benzothiadiazine-3-one 1,1-dioxide,
2-[3-[4-(2-methoxyphenyl)-1-piperazinyl]propyl]-3,4-dihydro-1,2,4-benzothiadiazine-3-one 1,1-dioxide,
2-[4-[4-(2-methoxyphenyl)-1-piperazinyl]butyl]-3,4-dihydro-1,2,4-benzothiadiazine-3-one 1,1-dioxide,
2-[2-[4-(2-methoxyphenyl)-1-piperazinyl]ethyl]-6,7-dimethoxy-3,4-dihydro-1,2,4-benzothiadiazine-3-one 1,1-dioxide,
2-[3-[4-(2-methoxyphenyl)-1-piperazinyl]propyl]-6,7-dimethoxy-3,4-dihydro-1,2,4-benzothiadiazine-3-one 1,1-dioxide,
2-[4-[4-(2-methoxyphenyl)-1-piperazinyl]butyl]-6,7-dimethoxy-3,4-dihydro-1,2,4-benzothiadiazine-3-one 1,1-dioxide,
2-[2-[4-(2-methoxyphenyl)-1-piperazinyl]ethyl]-6,7-methylenedioxy-3,4-dihydro-1,2,4-benzothiadiazine-3-one 1,1-dioxide,
2-[3-[4-(2-methoxyphenyl)-1-piperazinyl]propyl]-6,7-methylenedioxy-3,4-dihydro-1,2,4-benzothiadiazine-3-one 1,1-dioxide,
2-[4-[4-(2-methoxyphenyl)-1-piperazinyl]butyl]-6,7-methylenedioxy-3,4-dihydro-1,2,4-benzothiadiazine-3-one 1,1-dioxide,
2-[2-[4-(2-methoxyphenyl)-1-piperazinyl]ethyl]-6,7-dimethylenedioxy-3,4-dihydro-1,2,4-benzothiadiazine-3-one 1,1-dioxide,
2-[3-[4-(2-methoxyphenyl)-1-piperazinyl]propyl]-6,7-dimethylenedioxy-3,4-dihydro-1,2,4-benzothiadiazine-3-one 1,1-dioxide,
2-[4-[4-(2-methoxyphenyl)-1-piperazinyl]butyl]-6,7-dimethylenedioxy-3,4-dihydro-1,2,4-benzothiadiazine-3-one 1,1-dioxide,
2-[2-[4-(2-methoxyphenyl)-1-piperazinyl]ethyl]-6,7-trimethylenedioxy-3,4-dihydro-1,2,4-benzothiadiazine-3-one 1,1-dioxide, 2-[3-[4-(2-methoxyphenyl)-1-piperazinyl]propyl]-6,7-trimethylenedioxy-3,4-dihydro-1,2,4-benzothiadiazine-3-one 1,1-dioxide,
2-[4-[4-(2-methoxyphenyl)-1-piperazinyl]butyl]-6,7-trimethylenedioxy-3,4-dihydro-1,2,4-benzothiadiazine-3-one 1,1-dioxide,
2-[2-[4-(2-methoxyphenyl)-1-piperazinyl]ethyl]-5,6-methylenedioxy-3,4-dihydro-1,2,4-benzothiadiazine-3-one 1,1-dioxide,
2-[3-[4-(2-methoxyphenyl)-1-piperazinyl]propyl]-5,6-methylenedioxy-3,4-dihydro-1,2,4-benzothiadiazine-3-one 1,1-dioxide,
2-[4-[4-(2-methoxyphenyl)-1-piperazinyl]butyl]-5,6-methylenedioxy-3,4-dihydro-1,2,4-benzothiadiazine-3-one 1,1-dioxide,
2-[2-[4-(2-methoxyphenyl)-1-piperazinyl]ethyl]-5,6-dimethylenedioxy-3,4-dihydro-1,2,4-benzothiadiazine-3-one 1,1-dioxide,
2-[3-[4-(2-methoxyphenyl)-1-piperazinyl]propyl]-5,6-dimethylenedioxy-3,4-dihydro-1,2,4-benzothiadiazine-3-one 1,1-dioxide,
2-[4-[4-(2-methoxyphenyl)-1-piperazinyl]butyl]-5,6-dimethylenedioxy-3,4-dihydro-1,2,4-benzothiadiazine-3-one 1,1-dioxide,
2-[2-[4-(2-methoxyphenyl)-1-piperazinyl]ethyl]-5,6-trimethylenedioxy-3,4-dihydro-1,2,4-benzothiadiazine-3-one 1,1-dioxide,
2-[3-[4-(2-methoxyphenyl)-1-piperazinyl]propyl]-5,6-trimethylenedioxy-3,4-dihydro-1,2,4-benzothiadiazine-3-one 1,1-dioxide,
2-[4-[4-(2-methoxyphenyl)-1-piperazinyl]butyl]-5,6-trimethylenedioxy-3,4-dihydro-1,2,4-benzothiadiazine-3-one 1,1-dioxide,
2-[2-[4-(2-methoxyphenyl)-1-piperazinyl]ethyl]-4-methyl-3,4-dihydro-1,2,4-benzothiadiazine-3-one 1,1-dioxide,
2-[2-[4-(2-methoxyphenyl)-1-piperazinyl]ethyl]-6,7-dimethoxy-4-methyl-3,4-dihydro-1,2,4-benzothiadiazine-3-one 1,1-dioxide,
2-[2-[4-(2-methoxyphenyl)-1-piperazinyl]ethyl]-6,7-methylenedioxy-4-methyl-3,4-dihydro-1,2,4-benzothiadiazine-3-one 1,1-dioxide,
2-[2-[4-(2-methoxyphenyl)-1-piperazinyl]ethyl]-6,7-dimethylenedioxy-4-methyl-3,4-dihydro-1,2,4-benzothiadiazine-3-one 1,1-dioxide, and
2-[2-[4-(2-methoxyphenyl)-1-piperazinyl]ethyl]-6,7-trimethylenedioxy-5-methyl-3,4-dihydro-1,2,4-benzothiadiazine-3-one 1,1-dioxide.

Among the present compounds, the preferable compounds are as follows.
3-[2-[4-(2-methoxyphenyl)-1-piperazinyl]ethyl]-6,7-dimethoxy-1,2,3,4-tetrahydroquinazoline-2,4-dione,
3-[2-[4-(2-methoxyphenyl)-1-piperazinyl]ethyl]-6,7-dimethylenedioxy-1,2,3,4-tetrahydroquinazoline-2,4-dione,
3-[2-[4-(2-methoxyphenyl)-1-piperazinyl]ethyl]-6,7-trimethylenedioxy-1,2,3,4-tetrahydroquinazoline-2,4-dione,
3-[4-[4-(2-methoxyphenyl)-1-piperazinyl]butyl]-6,7-trimethylenedioxy-1,2,3,4-tetrahydroquinazoline-2,4-dione,
3-[2-[4-(2-methoxyphenyl)-1-piperazinyl]ethyl]-7-acetylamino-1,2,3,4-tetrahydroquinazoline-2,4-dione,
2-[2-[4-(2-methoxyphenyl)-1-piperazinyl]ethyl]-3,4-dihydro-1,2,4-benzothiadiazine-3-one 1,1-dioxide
2-[2-[4-(2-methoxyphenyl)-1-piperazinyl]ethyl]-6,7-dimethylenedioxy-3,4-dihydro-1,2,4-benzothiadiazine-3-one 1,1dioxide, and
2-[2-[4-(2-methoxyphenyl)-1-piperazinyl]ethyl]-6,7-trimethylenedioxy-3,4-dihydro-1,2,4-benzothiadiazine-3-one 1,1-dioxide.

The present invention also relates to the physiologically acceptable acid addition salt of the present compound of the general formula [I]. Such salts include those derived from organic and inorganic acids such as, without limitation, hydrochloric acid, hydrobromic acid, sulfuric acid, phosphoric acid, nitric acid, acetic acid, succinic acid, adipic acid, propionic acid, tartaric acid, fumaric acid, maleic acid, oxalic acid, citric acid, benzoic acid, toluenesulfonic acid, methanesulfonic acid and the like.

According to the present invention, the foregoing compounds can be prepared as follows.

The compound of the formula [II]:

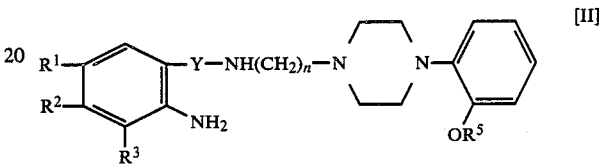

wherein $R^1$, $R^2$, $R^3$, $R^5$, Y and n are as herein defined, is reacted with urea while heating to obtain the present compound. The above reaction proceeds in the absence of the solvent, but the presence of the inert solvent such as dimethylformamide, dimethylsulfoxide, N-methylpyrrolidone, tetrahydrofuran, dioxane, alcohol, water and the like is no obstacle.

The compound of the formula [II] may be condensed with trichloromethyl chloroformate to form ring, thereby the present compound being obtained.

Alternatively, the present compound can be obtained by reacting the compound of the formula [III]:

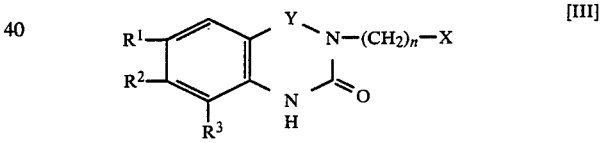

wherein $R^1$, $R^2$, $R^3$, Y and n are as herein defined and X is halogen atom, with 1-(o-alkoxyphenyl)piperazine represented by the formula [IV]:

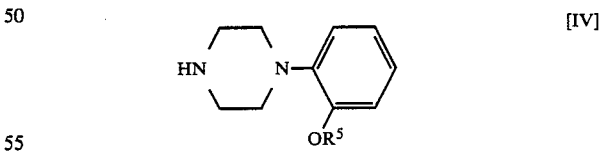

wherein $R^5$ is as herein defined, in the inert solvent. The reaction temperature is not particularly limited and is generally in the range of between room temperature and about 150° C. To smoothly proceed the reaction, it is preferable to add 1-(o-alkoxyphenyl)piperazine in excess and/or to add a scavenger for hydrogen halide produced in the course of the reaction such as inorganic base, for example potassium carbonate and sodium carbonate and tertiary organic amine, for example triethylamine.

Further, the present compound can be prepared by reacting the compound of the formula [V]:

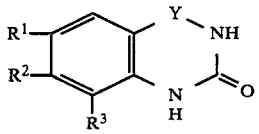

wherein $R^1$, $R^2$, $R^3$ and Y are as herein defined, with the compound of the formula [VI]:

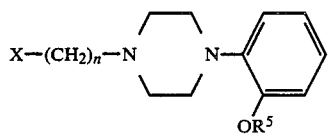

wherein $R^5$, n and X are as herein defined, in the inert solvent. The reaction temperature is particularly unlimited and is generally in the range of between room temperature and about 100° C. In advance of the above-mentioned reaction, it is preferable to convert the compound of the formula [V] into its metal salt by reacting with metal hydride, metal alkoxide and the like in the inert solvent.

When the present compound of the general formula [I] wherein $R^4$ is alkyl group of 1 to 3 carbon atoms and the others are as herein defined is desired, phenylpiperazine of the general formula [I] wherein $R^4$ is hydrogen atoms and the others are as herein defined is converted into its metal salt in the manner as above followed by reacting with alkyl halide. The reaction is generally carried out in the temperature of between room temperature and about 150° C.

After the conclusion of the reaction, the product is purified in accordance with any conventional purification method such as recrystallization and chromatography.

And, the acid addition salt of the present compound may be prepared by neutralizing the compound of the formula [I] with the desired acid in accordance with the conventional method.

The present compounds including the acid addition salt thereof show the ability to reduce blood pressure and a low acute toxicity, as will be shown in Examples. Accordingly, the present compounds are highly desirable as pharmaceutical agents to be used in the treatment of hypertension.

Pharmaceutical composition for effecting such a treatment will contain one of the present compound in combination with a pharmaceutical carrier which is nontoxic, inert and pharmaceutically acceptable. Other pharmaceutically active ingredients may be incorporated in the composition. Such pharmaceutical compositions are preferably in dosage unit form.

Although the dosage must in each case be carefully adjusted considering the age, weight and condition of the recipient, the route of administration, the nature and gravity of the illness, the kinds and frequency of the other treatment if any, generally the daily dose will be from 0.1 to 100 mg/kg of body weight. The preferable daily dose is 1 to 30 mg/kg of body weight. In some instances a sufficient therapeutic effect can be obtained at lower doses while in others, larger doses will be required.

Oral administration can be effected utilizing solid and liquid dosage unit forms such as powders, tablets, dragees, capsules, granulates, suspensions, solutions, syrups and the like.

Oral solids such as powders, tablets and so on can be prepared in dosage unit form so as to contain 5 to 95% by weight, preferably 25 to 90% by weight, that is, 5 to 500 mg, preferably 25 to 250 mg of the present compound as an active ingredient.

Powders are prepared by comminuting the present compound to a suitable fine size and mixing with a similarly comminuted pharmaceutical solid carrier such as starch, lactose, sucrose, glucose or mannitol. Any conventional adjuvants such as sweetening, flavoring, preservative, dispersing and coloring agents can be present.

Capsules are made by preparing a powder mixture as described above and filling formed gelatin sheaths. The adjuvants mentioned above can also be added to the powder mixture before the filling operation and other adjuvants such as a disintegrating or solubilizing agent to improve the availability of the medicament when the capsule is ingested may be added.

Tablets are formulated for example by preparing a powder mixture, granulating, adding any adjuvants and pressing into tablets Oral fluids such as solutions, syrups, suspensions and so on can be prepared in dosage unit form so as to contain 0.5 to 10% by weight of the present compound as an active ingredient. Suspensions can be formulated by dispersing the present compound in a nontoxic pharmaceutical liquid carrier. Any conventional adjuvants such as solubilizers, emulsifiers, preservatives, flavor and the like can also be present.

Parenteral administration can be effected utilizing liquid dosage unit forms such as sterile solutions and suspensions intended for subcutaneous, intramuscular, intravenous or intraperitoneal injection. These are prepared by suspending or dissolving a measured amount of the present compound in a nontoxic liquid vehicle suitable for injection such as a physiological saline solution, solution of sucrose such as dextrose and the like, solution of glycols such as propylene glycol and ethylene glycol. Especially, the injection including physiological saline solution as the vehicle contains 0.5 to 20% by weight, more preferably 1 to 10% by weight of the present compound as the active ingredient.

The following examples will serve to further understand the present invention through the presentation of specific embodiments. These examples should not be construed as a limitation on the scope of the invention since the subject matter regarded as the invention is set forth in the appended claims.

EXAMPLE 1

3-[2-[4-(2-methoxyphenyl)-1-piperazinyl]ethyl]-6,7-dimethoxy-1,2,3,4-tetrahydroquinazoline-2,4-dione
(Compound No. 1)

Two grams of 6,7-dimethoxy-1,2,3,4-tetrahydroquinazoline-2,4-dione was dissolved in 30 ml of dimethylformamide. After adding 1230 mg of sodium hydride thereto under cooling, the mixture was stirred for 10 minutes. Then, 23 grams of 2-[4-(2-methoxyphenyl)-1-piperazinyl]ethyl chloride was added and the stirring was continued at 70° C. for 6 hours. After the reaction was finished, water was added to the reaction mixture and the mixture was extracted with chloroform and concentrated. The resultant residue was purified through the silica gel chromatography and crystallized from methanol to obtain 1.4 g of the titled compound (yield: 35%).

The characteristics of this compound were shown in Table 1. And, IR spectrum of this compound was shown in FIG. 1 of the accompanying drawings.

EXAMPLE 2

3-[2-[4-(2-methoxyphenyl)-1-piperazinyl]ethyl]-6,7-trimethylenedioxy-1,2,3,4-tetrahydroquinazoline-2,4-dione (Compound No. 2)

Forty-two milliliters of triethylamine was added to 6.0 g of 3-(2-chloroethyl)-6,7-trimethylenedioxy-1,2,3,4-tetrahydroquinazoline-2,4-dione, 5.8 g of 4-(2-methoxyphenyl)piperazine and 60 ml of dimethylformamide to react at 90° C. for 26 hours. The resultant reaction liquid was concentrated and crystallized from methanol to obtain 7.4 g of the titled compound (yield: 81%).

Figure 2:
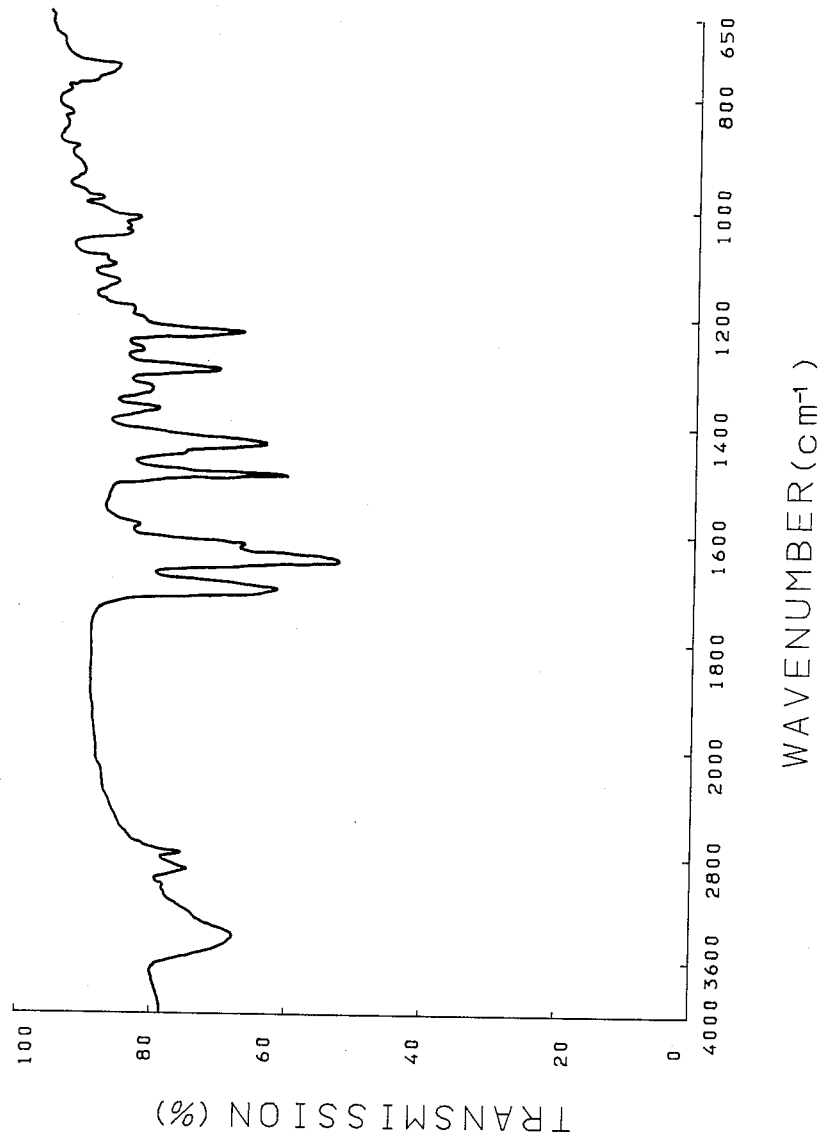

The characteristics of this compound were shown in Table 1. And, IR spectrum of this compound was shown in FIG. 2 of the accompanying drawings.

Figure 3:
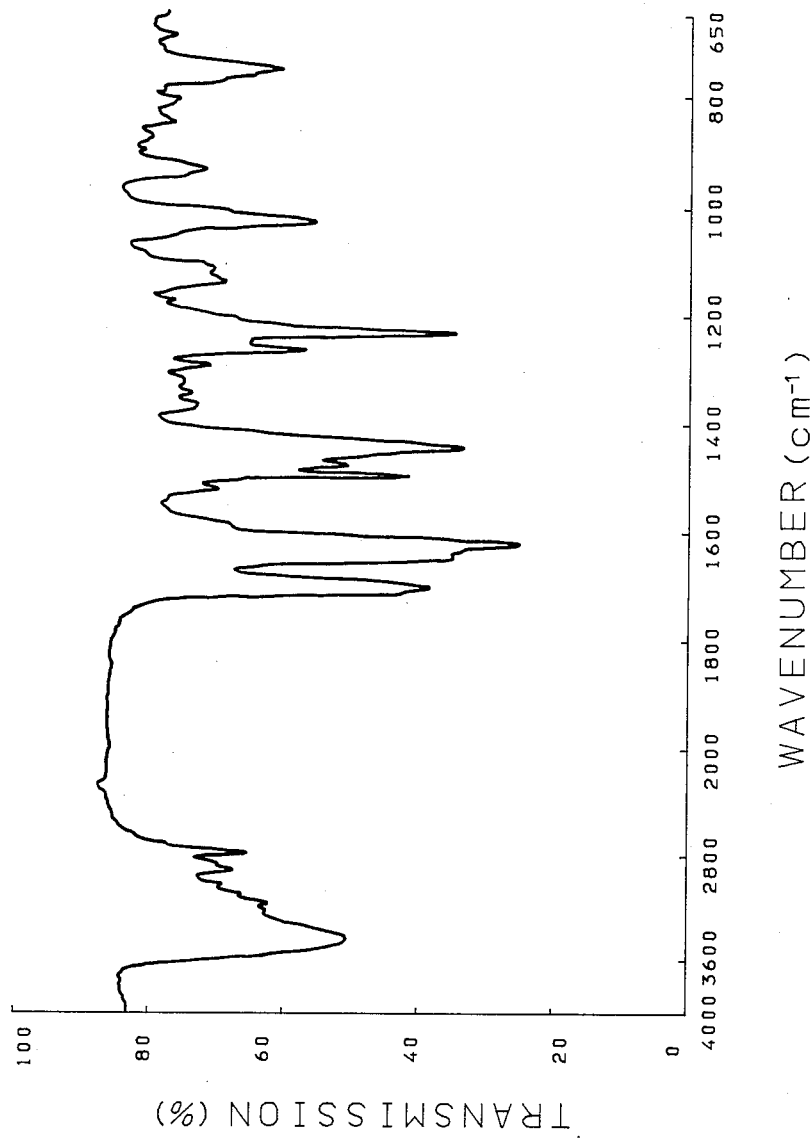
Figure 4:
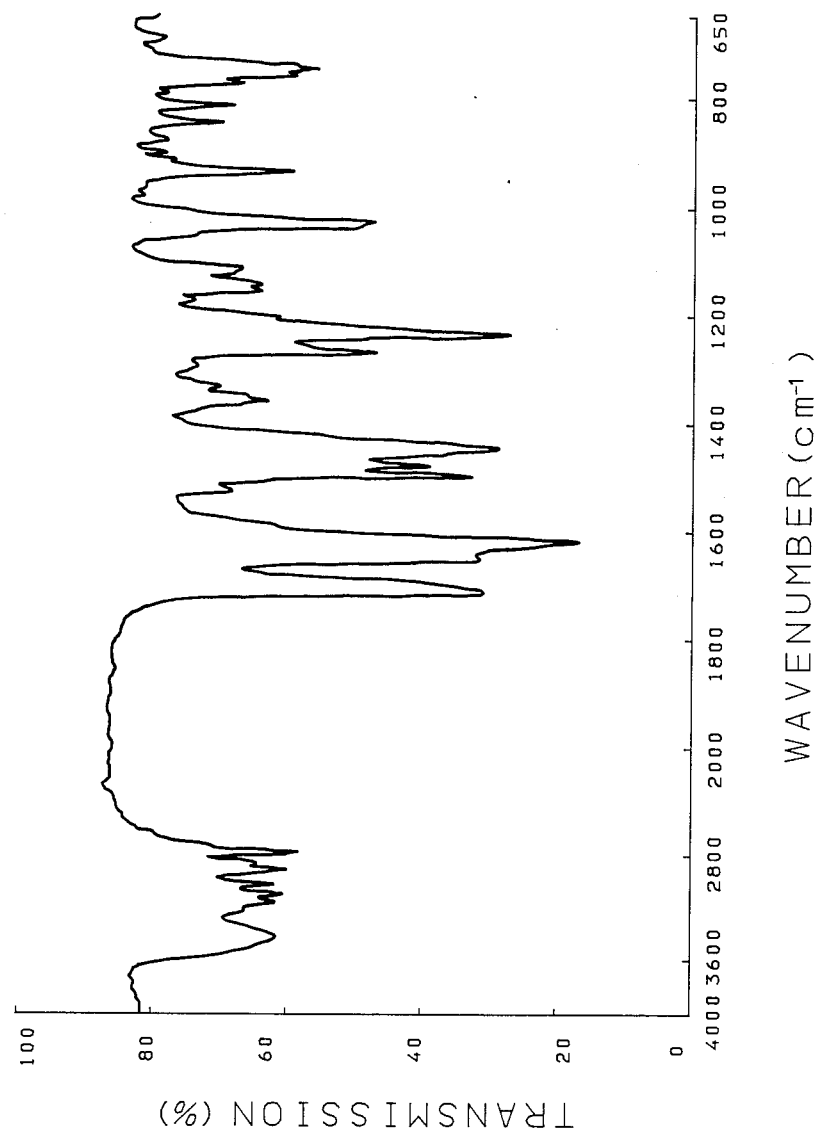
Figure 5:
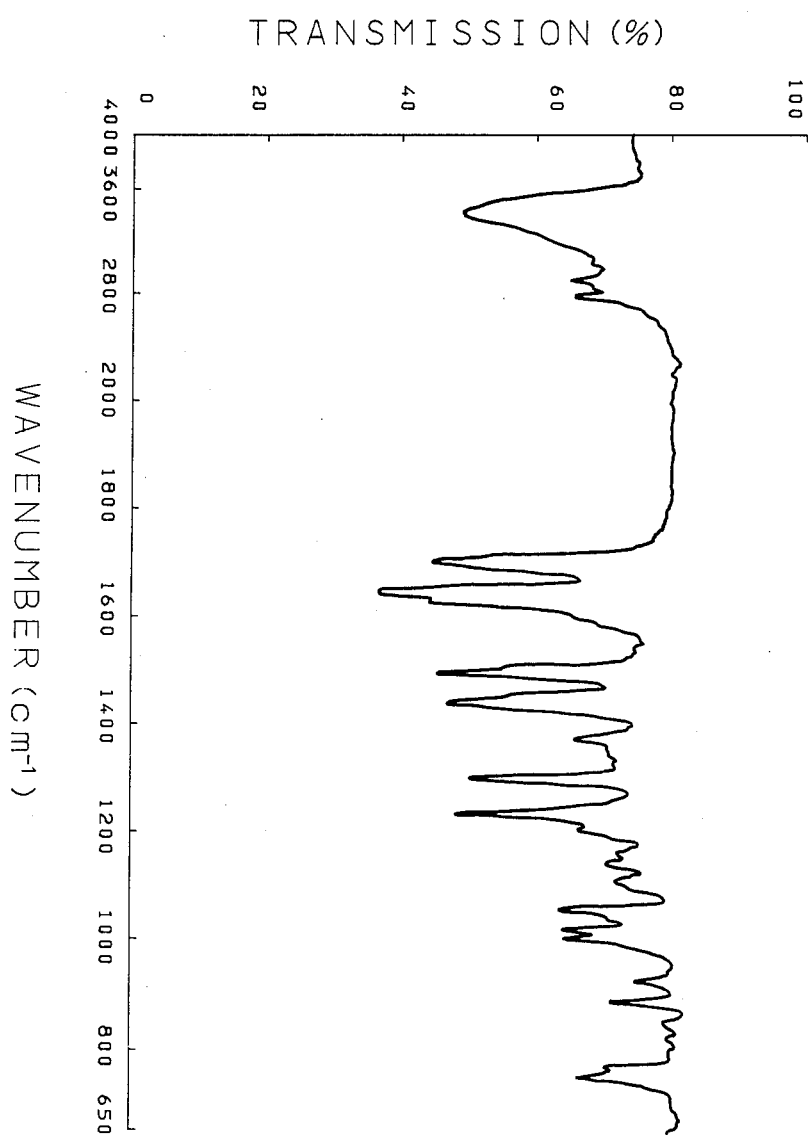
Figure 6:
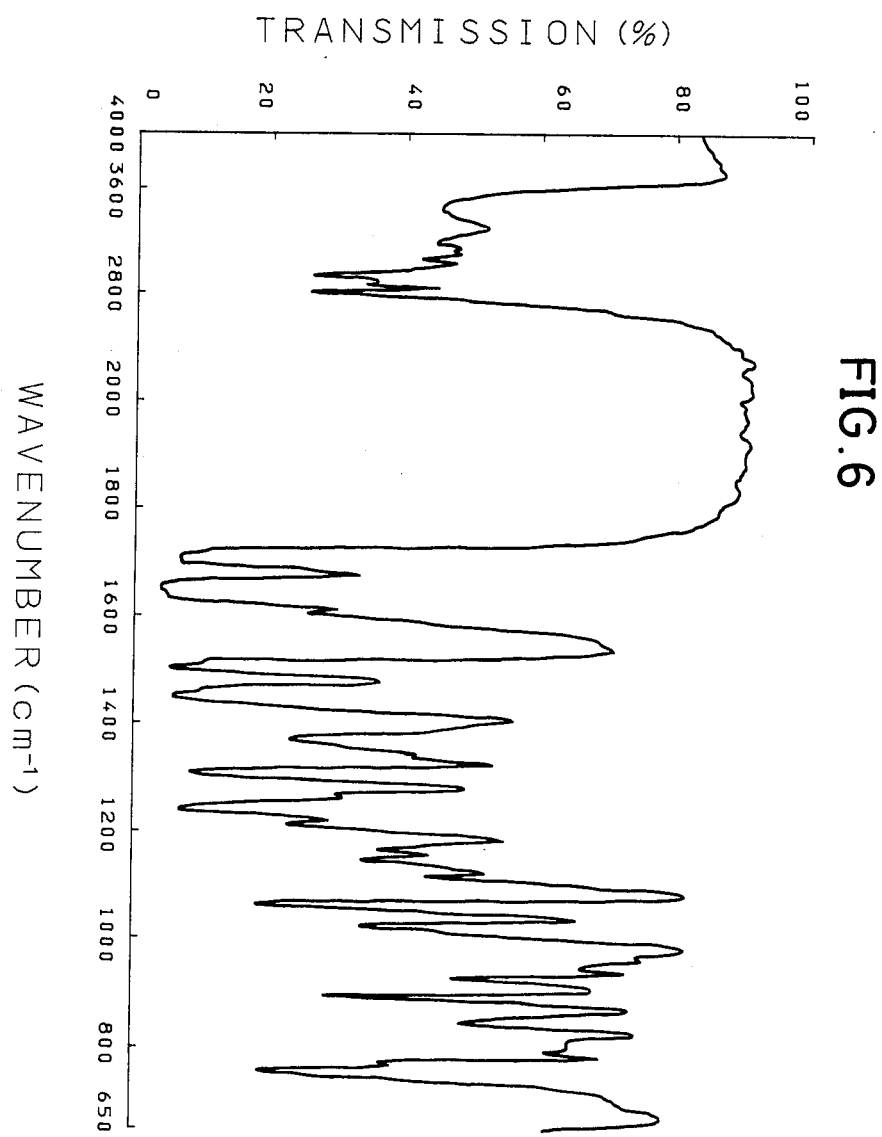

In the similar manner, 3-[2-[4-(2-methoxyphenyl)-1-piperazinyl]ethyl]-6,7-methylenedioxy-1,2,3,4-tetrahydroquinazoline-2,4-dione (Compound No. 3), 3-[3-[4-(2-methoxyphenyl)-1-piperazinyl]propyl]-6,7-methylenedioxy-1,2,3,4-tetrahydroquinazoline-2,4-dione (Compound No. 4), 3-[2-[4-(2-methoxyphenyl)-1-piperazinyl]ethyl]-6,7-dimethylenedioxy-1,2,3,4-tetrahydroquinazoline-2,4-dione (Compound No. 5), 3-[3-[4-(2-methoxyphenyl)-1-piperazinyl]propyl]-6,7-dimethylenedioxy-1,2,3,4-tetrahydroquinazoline-2,4-dione (Compound No. 6), 3-[3-[4-(2-methoxyphenyl)-1-piperazinyl]propyl]-6,7-trimethylenedioxy-1,2,3,4-tetrahydroquinazoline-2,4-dione (Compound No. 7) and 3-[4-[4-(2-methoxyphenyl)-1-piperazinyl]butyl]-6,7-trimethylenedioxy-1,2,3,4-tetrahydroquinazoline-2,4-dione (Compound No. 8) were prepared, whose characteristics being also shown in Table 1. And, IR spectrum of each of the compounds was shown in Figure of the accompanying drawings (Compound No. 3: FIG. 3, Compound No. 4: FIG. 4, Compound No. 5: FIG. 5, and Compound No. 6: FIG. 6).

EXAMPLE 3

2-[2-[4-(2-methoxyphenyl)-1-piperazinyl]ethyl]-6,7-dimethoxy-3,4-dihydro-1,2,4-benzothiadiazine-3-one 1,1-dioxide (Compound No. 10)

One gram and a half of 6,7-dimethoxy-3,4-dihydro-1,2,4-benzothiadiazine-3-one 1,1-dioxide was dissolved in 10 ml of dimethylformamide. After adding 280 mg of sodium hydride in 50% oil, the mixture was heated to 80° C. Then, a solution of 1.5 g of 2-[4-(2-methoxyphenyl)-1-piperazinyl]ethyl chloride in 5 ml of dimethylformamide was added dropwise to the resultant reaction liquid. After the addition was finished, the stirring was continued for 5 hours while heating at 80° C. to react. The resultant reaction mixture was poured into water to precipitate crystals. The produced crystals were filtered off followed by recrystallizing from methanol to obtain 1.0 g of the titled compound (yield: 36%).

Figure 7:
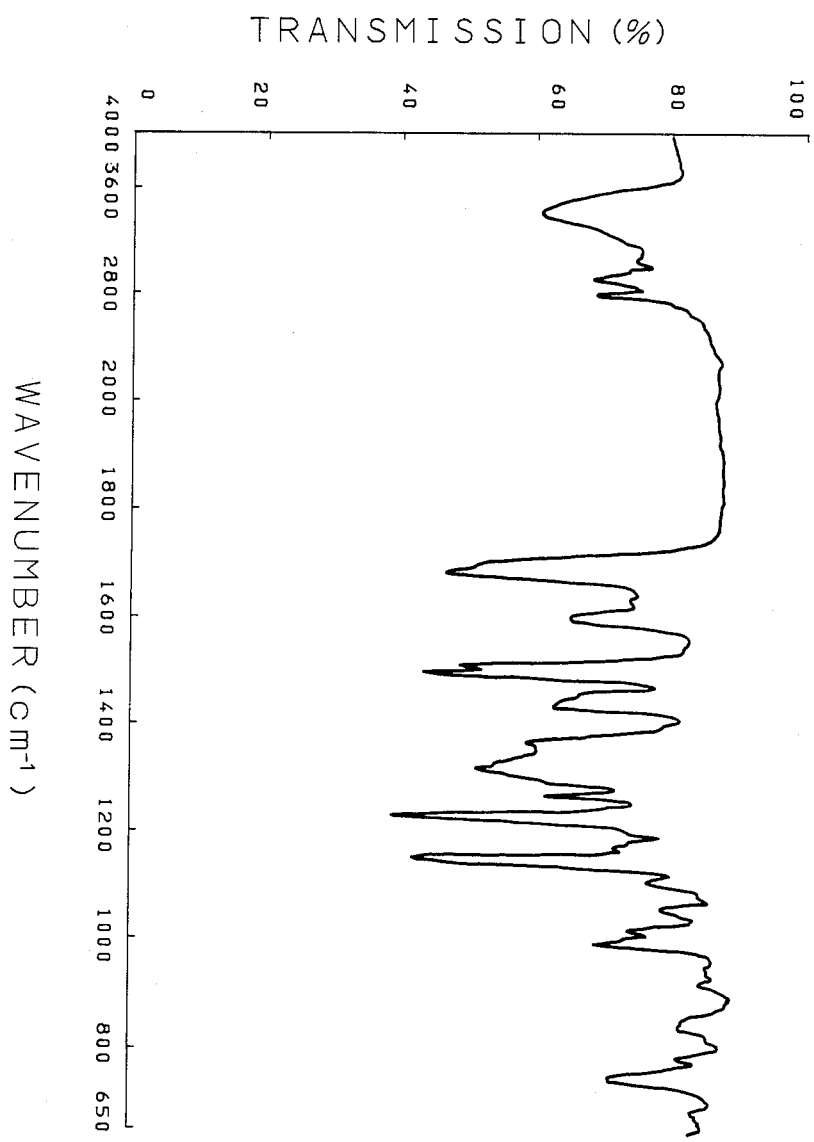

The characteristics of this compound were shown in Table 1. And, IR spectrum of this compound was shown in FIG. 7 of the accompanying drawings.

EXAMPLE 4

2-[2-[4-(2-methoxyphenyl)-1-piperazinyl]ethyl]-6,7-trimethylenedioxy-3,4-dihydro-1,2,4-benzothiadiazine-3-one 1,1-dioxide (Compound No. 12)

Thirty-two grams of N-[2-[4-(2-methoxyphenyl)-1piperazinyl]-ethyl]-2-amino-4,5-trimethylenedioxy-benzenesulfonamide and 15.4 ml of triethylamine were dissolved in 350 ml of methylene chloride. The thus-prepared solution was added dropwise to a solution of 4.2 ml of trichloromethyl chloroformate in 140 ml of methylene chloride at a temperature of not more than 5° C. After the addition was finished, the temperature was slowly increased to room temperature and the stirring was continued for one hour. Then, water saturated with sodium bicarbonate was added thereto and the stirring was continued for 30 minutes. The reaction mixture after drying methylene chloride over anhydrous sodium sulfate was concentrated and the resultant residue was purified through the silica gel chromatography and crystallized from ethanol to obtain 24.7 g of the titled compound (yield: 73.1%).

Figure 8:
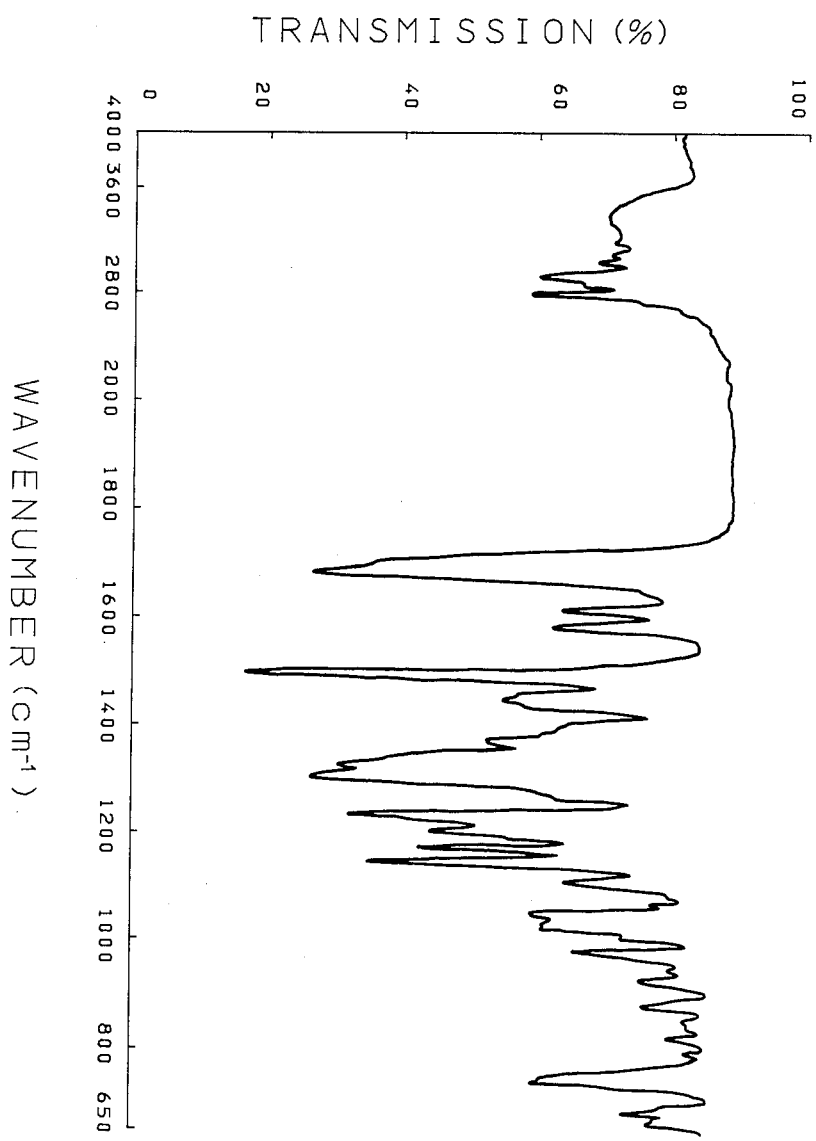

The characteristics of this compound were shown in Table 1. And, IR spectrum of this compound was shown in FIG. 8 of the accompanying drawings.

In the similar manner, 2-[2-[4-(2-methoxyphenyl)-1-piperazinyl]ethyl]-3,4-dihydro-1,2,4-benzothiadiazine-3-one 1,1-dioxide dihydrochloride (Compound No. 9), 2-[2-[4-(2-methoxyphenyl)-1-piperazinyl]ethyl-6,7-dimethylenedioxy-3,4-dihydro-1,2,4-benzothiadiazine-3-one 1,1-dioxide (Compound No 11), 2-[3-[4-(2-methoxyphenyl)-1-piperazinyl]propyl]-6,7-trimethylenedioxy-3,4-dihydro-1,2,4-benzothiadiazine-3-one 1,1-dioxide dihydrochloride (Compound No. 13) and 2-[2-[4-(2-methoxyphenyl)-1-piperazinyl]ethyl]-5,6-trimethylenedioxy-3,4-dihydro-1,2,4-benzothiadiazine-3-one 1,1-dioxide (Compound No. 14) were prepared, whose characteristics being also shown in Table 1.

Figure 9:
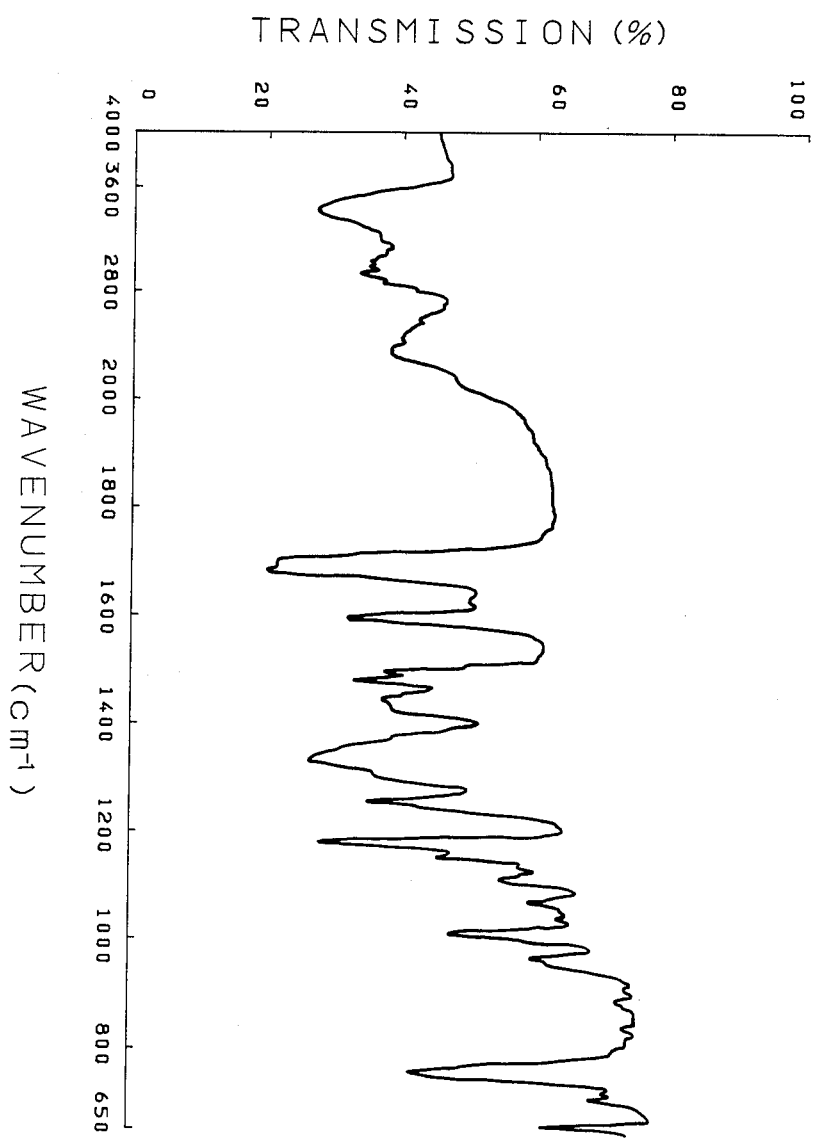
Figure 10:
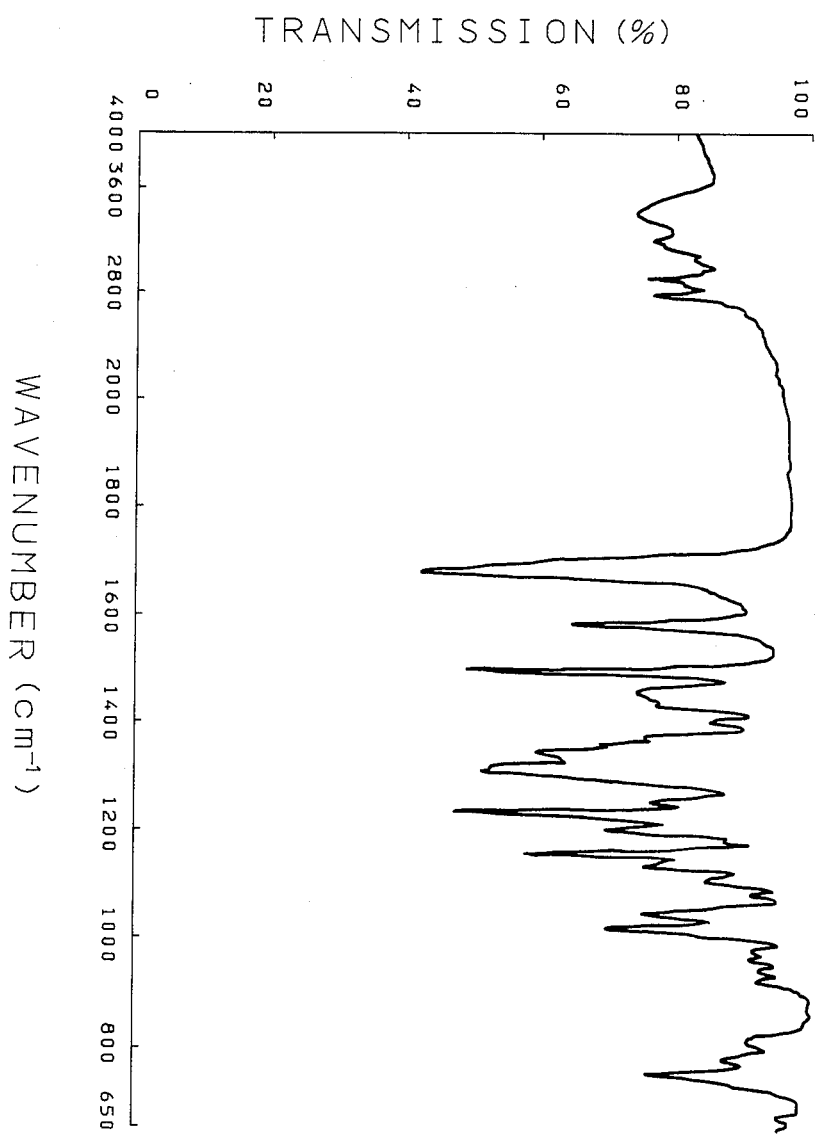

And, IR spectrum of each of the compounds was shown in Figure of the accompanying drawings (Compound No. 9: FIG. 9, and Compound No. 14: FIG. 10).

EXAMPLE 5

3-[2-[4-(2-methoxyphenyl)-1-piperazinyl]ethyl]-7-amino-1,2,3,4-tetrahydroquinazoline-2,4-dione (Compound No. 15)

Four hundred miligrams of sodium carbonate was added to 1.5 g of 7-amino-3-(2-chloroethyl)-1,2,3,4-tetrahydroquinazoline-2,4-dione, 1.4 g of 1-(2-methoxyphenyl)piperazine and 1.4 ml of dimethylformamide to react at 80° C. for 50 hours. The reaction liquid was concentrated and the resultant residue was purified through the silica gel chromatography to obtain 0.95 g of the titled compound (yield: 38%).

Figure 11:
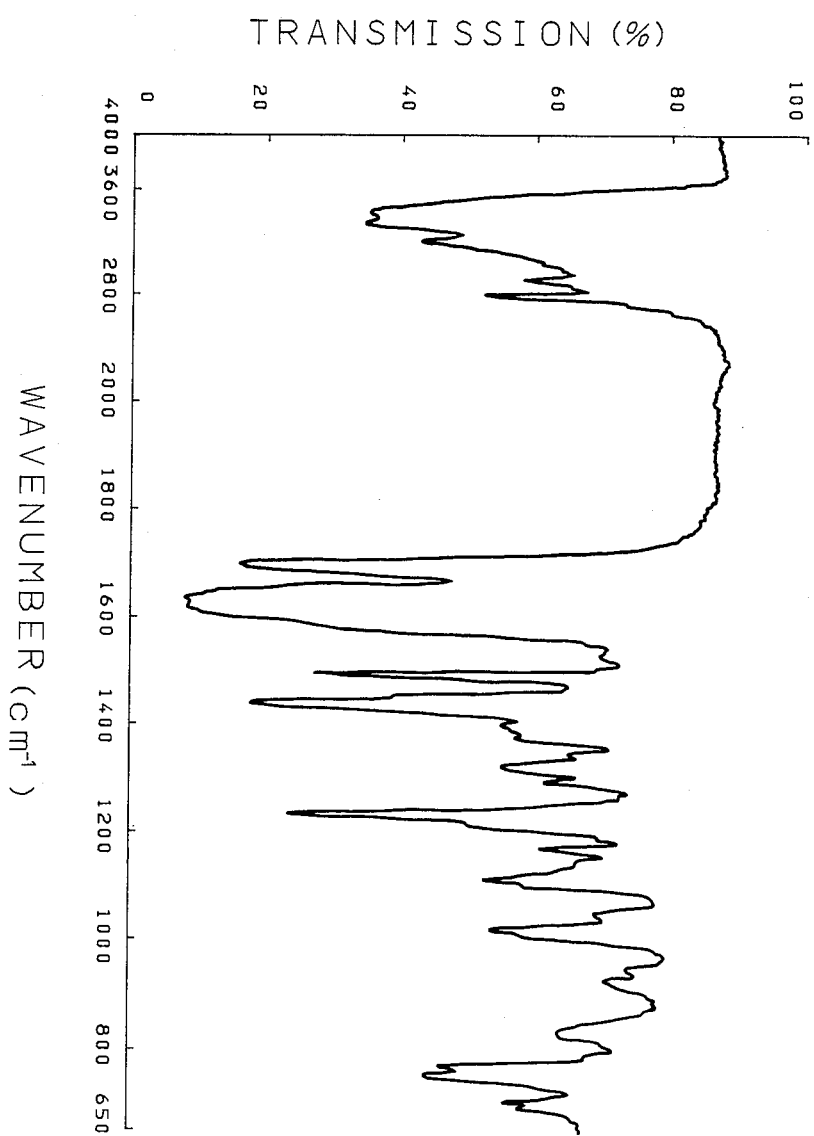

The characteristics of this compound were shown in Table 1. And, IR spectrum of this compound was shown in FIG. 11 of the accompanying drawings.

EXAMPLE 6

3-[2-[4-(2-methoxyphenyl)-1-piperazinyl]ethyl]-7-acetylamino-1,2,3,4-tetrahydroquinazoline-2,4-dione (Compound No. 17)

Four hundred and forty miligrams of urea was added to 1.5 g of 1-(2-methoxyphenyl)-4-[2-(4-acetylamino-2-aminobenzoyl)aminoethyl]piperazine to react at 160° C. for 8 hours. The reaction liquid was extracted with chloroform and purified through the silica gel chromatography to obtain 0.96 g of the titled compound (yield: 60%).

Figure 12:
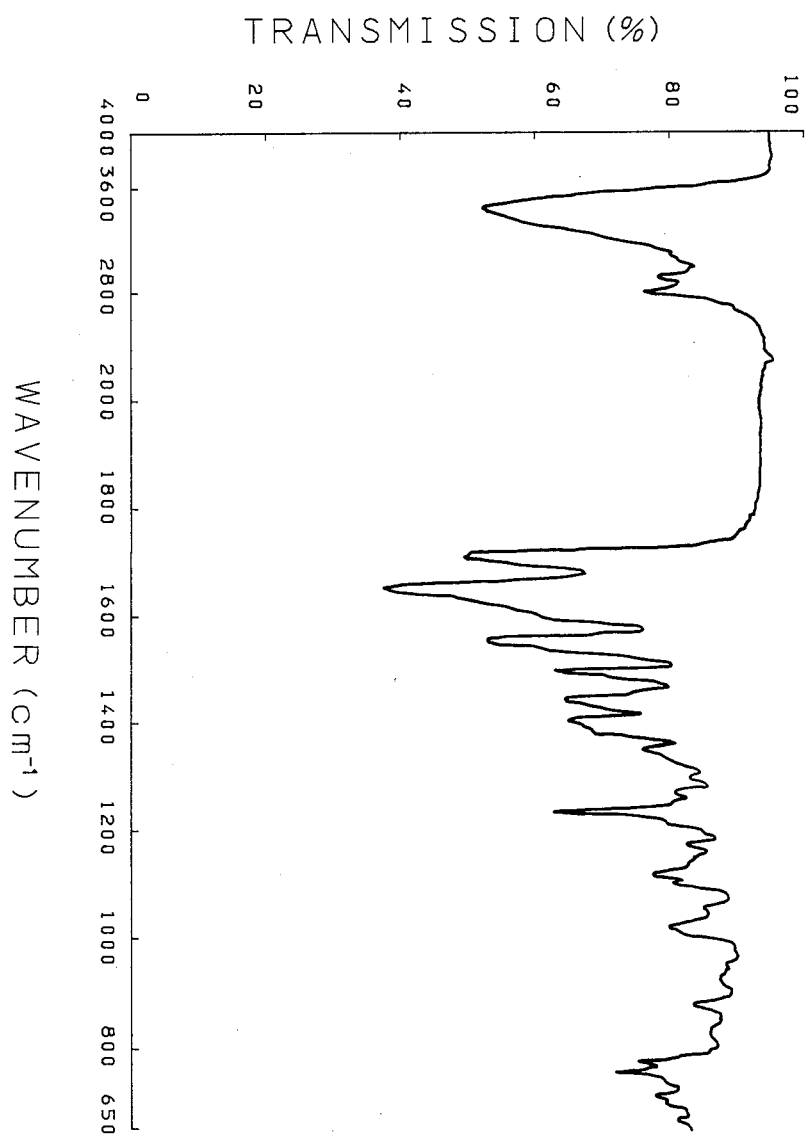

The characteristics of this compound were shown in Table 1. And IR spectrum of this compound was shown in FIG. 12 of the accompanying drawings.

Figure 13:
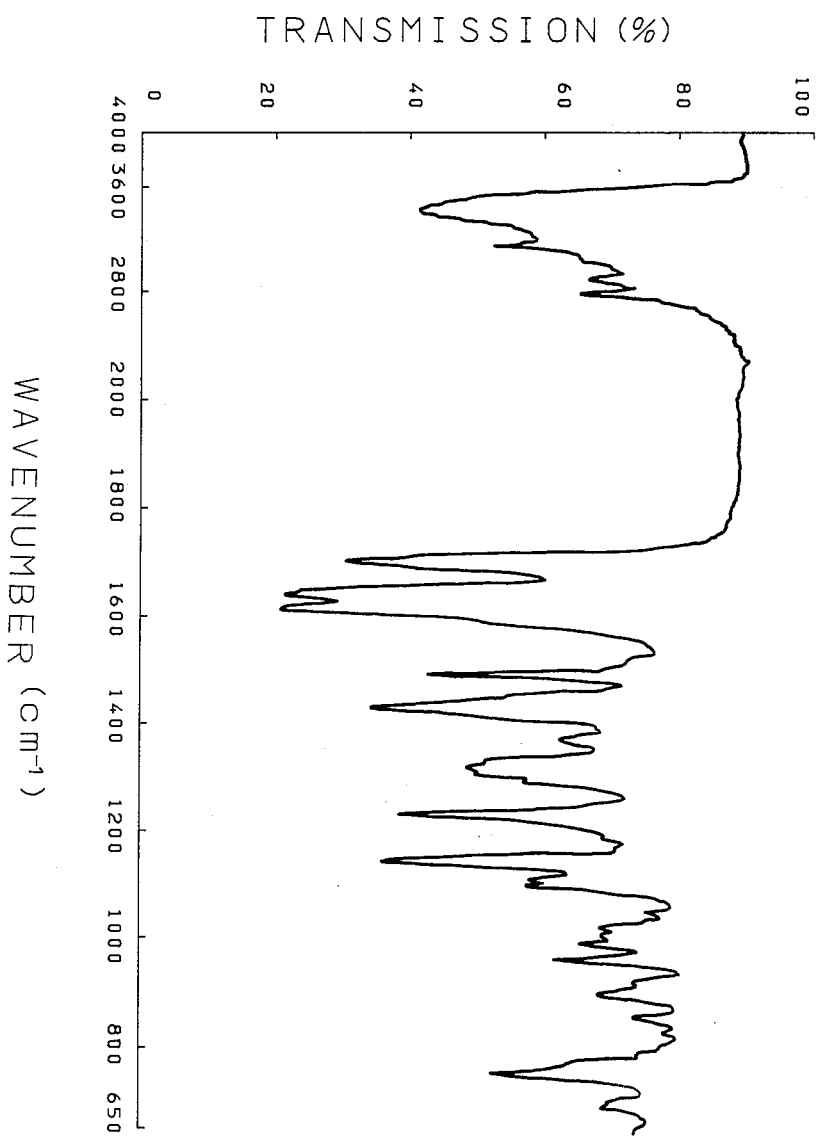

In the similar manner, 3-[2-[4-(2-methoxyphenyl)-1-piperazinyl]ethyl]-7-methanesulfonylamino-1,2,3,4-tetrahydroquinazoline-2,4-dione (Compound No. 16), 3-[2-[4-(2-methoxyphenyl)-1-piperazinyl]ethyl]-7-carbamoylamino-1,2,3,4-tetrahydroquinazoline-2,4-dione (Compound No. 18), 3-[2-[4-(2-methoxyphenyl)-1-piperazinyl]ethyl]-6-methoxy-7-acetylamino-1,2,3,4-tetrahydroquinazoline-2,4-dione (Compound No. 19) and 3-[2-[4-(2-methoxyphenyl)-1-piperazinyl]ethyl]-6-acetylamino-7-methoxy-1,2,3,4-tetrahydroquinazoline-2,4-dione (Compound No. 20) were prepared, whose characteristics being also shown in Table 1. And, IR spectrum of the compound (Compound No. 16) was shown in FIG. 13 of the accompanying drawings.

EXAMPLE 7

3-[2-[4-(2-methoxyphenyl)-1-piperazinyl]ethyl]-6,7-trimethylenedioxy-1-methyl-1,2,3,4-tetrahydroquinazoline-2,4-dione (Compound No. 21)

Eight hundred and thirty miligrams of 3-[2-[4-(2-methoxyphenyl)-1-piperazinyl]ethyl]-6,7-trimethylenedioxy-1,2,3,4-tetrahydroquinazoline-2,4-dione was dissolved in 15 ml of dimethylformamide and 100 mg of sodium hydride in 50% oil was added thereto followed by stirring for 30 minutes. Then, the reaction liquid was warmed to 60° C. and 0.13 ml of methyl iodide was added thereto followed by stirring for 1 hour. The reaction liquid was extracted with ethyl acetate and the extract was washed successively with water and water saturated with sodium chloride and dried over anhydrous sodium sulfate. The solvent was distilled away and the resultant residue was purified through the silica gel chromatography and crystallized from ethanol to obtain 640 mg of the titled compound (yield: 74.8%).

In the similar manner, 3-[2-[4-(2-methoxyphenyl)-1-piperazinyl]ethyl]-6,7-dimethylenedioxy-1-methyl-1,2,3,4-tetrahydroquinazoline-2,4-dione (Compound No. 22), 2-[2-[4-(2-methoxyphenyl)-1-piperazinyl]ethyl]-6,7-trimethylenedioxy-4-methyl-3,4-dihydro-1,2,4-benzothiadiazine-3-one 1,1-dioxide (Compound No. 23), 3-[2-[4-(2-methoxyphenyl)-1-piperazinyl]ethyl]-6,7-trimethylenedioxy-1-ethyl-1,2,3,4-tetrahydroquinazoline-2,4-dione dihydrochloride (Compound No. 24) and 3-[2-[4-(2-methoxyphenyl)-1-piperazinyl]ethyl]-6,7-trimethylenedioxy-1-propyl-1,2,3,4-tetrahydroquinazoline-2,4-dione dihydrochloride (Compound No. 25) were prepared, whose characteristics being also shown in Table 1.

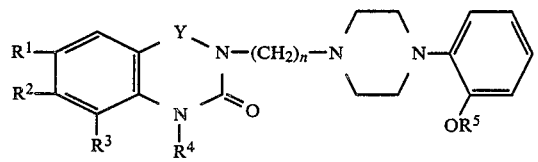

| Compound No. | R$^1$ | R$^2$ | R$^3$ | R$^4$ | R$^5$ | Y | n | salt | melting point (°C.) | | C (%) | H (%) | N (%) |
|---|---|---|---|---|---|---|---|---|---|---|---|---|---|
| 1 | —OCH$_3$ | —OCH$_3$ | H | H | —CH$_3$ | —C(=O)— | 2 | — | 250–252 | calcd. | 62.71 | 6.41 | 12.72 |
|   |   |   |   |   |   |   |   |   |   | found | 62.35 | 6.23 | 12.55 |
| 2 | —O(CH$_2$)$_3$O— | " | " | " | " | " | " | — | 208–210 | calcd. | 63.70 | 6.24 | 12.38 |
|   |   |   |   |   |   |   |   |   |   | found | 63.44 | 6.13 | 12.28 |
| 3 | —OCH$_2$O— | " | " | " | " | " | " | — | 242–244 | calcd. | 62.25 | 5.70 | 13.20 |
|   |   |   |   |   |   |   |   |   |   | found | 62.64 | 5.64 | 13.23 |
| 4 | —OCH$_2$O— | " | " | " | " | " | 3 | — | 226–228 | calcd. | 63.00 | 5.98 | 12.78 |
|   |   |   |   |   |   |   |   |   |   | found | 63.10 | 6.11 | 12.74 |
| 5 | —O(CH$_2$)$_2$O— | " | " | " | " | " | 2 | — | 235–237 | calcd. | 63.00 | 5.98 | 12.78 |
|   |   |   |   |   |   |   |   |   |   | found | 63.03 | 6.01 | 12.73 |
| 6 | —O(CH$_2$)$_2$O— | " | " | " | " | " | 3 | — | 209–211 | calcd. | 63.70 | 6.24 | 12.38 |
|   |   |   |   |   |   |   |   |   |   | found | 63.38 | 6.17 | 12.14 |
| 7 | —O(CH$_2$)$_3$O— | " | " | " | " | " | 3 | — | 215–217 | calcd. | 64.36 | 6.48 | 12.01 |
|   |   |   |   |   |   |   |   |   |   |        | 64.38 | 6.75 | 12.30 |
| 8 | —O(CH$_2$)$_3$O— | " | " | " | " | " | 4 | — | 194–196 | calcd. | 64.98 | 6.71 | 11.66 |
|   |   |   |   |   |   |   |   |   |   | found | 65.07 | 6.73 | 11.65 |
| 9 | H | H | " | " | " | O$_2$—S— | 2 | 2HCl | 187–190 | calcd. | 49.08 | 5.35 | 11.45 |
|   |   |   |   |   |   |   |   |   |   | found | 49.31 | 5.51 | 11.33 |
| 10 | —OCH$_3$ | —OCH$_3$ | " | " | " | " | " | — | 251–254 | calcd. | 55.45 | 5.92 | 11.76 |
|   |   |   |   |   |   |   |   |   |   | found | 55.23 | 6.05 | 11.56 |
| 11 | —O(CH$_2$)$_2$O— | " | " | " | " | " | " | — | 205–206 | calcd. | 55.69 | 5.52 | 11.81 |
| 12 | —O(CH$_2$)$_3$O— | " | " | " | " | " | " | — | 172.5–173.5 | calcd. | 56.54 | 5.78 | 11.47 |
|   |   |   |   |   |   |   |   |   |   | found | 56.35 | 5.80 | 11.43 |
| 13 | —O(CH$_2$)$_3$O— | " | " | " | " | " | 3 | dihydrochloride | 157–162 | calcd. | 50.09 | 5.60 | 9.74 |
|   |   |   |   |   |   |   |   |   |   | found | 49.72 | 5.48 | 9.59 |
| 14 | H | —O(CH$_2$)$_3$O— | " | " | " | " | 2 | — | 196–198 | calcd. | 56.54 | 5.78 | 11.47 |
|   |   |   |   |   |   |   |   |   |   | found | 56.20 | 5.73 | 11.08 |
| 15 | " | —NH$_2$ | H | " | " | —C(=O)— | " | — | 260–262 | calcd. | 63.78 | 6.37 | 17.71 |
|   |   |   |   |   |   |   |   |   |   | found | 63.72 | 6.35 | 17.67 |

-continued

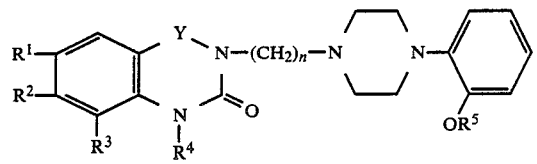

| Compound No. | $R^1$ | $R^2$ | $R^3$ | $R^4$ | $R^5$ | Y | n | salt | melting point (°C.) | | C (%) | H (%) | N (%) |
|---|---|---|---|---|---|---|---|---|---|---|---|---|---|
| 16 | " | —NHSO$_2$CH$_3$ | " | " | " | " | " | — | 263–265 | calcd. | 55.80 | 5.75 | 14.79 |
| | | | | | | | | | | found | 55.82 | 5.73 | 14.73 |
| 17 | " | —NHCCH$_3$ ‖ O | " | " | " | " | " | — | 252–257 | calcd. | 63.14 | 6.22 | 16.01 |
| | | | | | | | | | | found | 63.15 | 6.20 | 16.03 |
| 18 | " | —NHCNH$_2$ ‖ O | " | " | " | " | " | — | 271–276 | calcd. | 60.26 | 5.98 | 19.17 |
| | | | | | | | | | | found | 60.21 | 5.99 | 19.15 |
| 19 | —OCH$_3$ | —NHCCH$_3$ ‖ O | " | " | " | " | " | — | 251–255 | calcd. | 61.66 | 6.25 | 14.98 |
| | | | | | | | | | | found | 61.61 | 6.22 | 14.97 |
| 20 | —NHCCH$_3$ ‖ O | —OCH$_3$ | " | " | " | " | " | — | 284–290 | calcd. | 61.16 | 6.25 | 14.98 |
| | | | | | | | | | | found | 61.10 | 6.21 | 14.95 |
| 21 | —O(CH$_2$)$_3$O— | | " | —CH$_3$ | " | " | " | — | 133–135 | calcd. | 64.36 | 6.48 | 12.01 |
| | | | | | | | | | | found | 64.10 | 6.45 | 11.99 |
| 22 | —O(CH$_2$)$_2$O— | | " | " | " | " | " | — | 171–172 | calcd. | 63.70 | 6.24 | 12.38 |
| | | | | | | | | | | found | 63.50 | 6.17 | 12.37 |
| 23 | —O(CH$_2$)$_3$O— | | " | " | " | O$_2$ —S— | " | — | 131–132 | calcd. | 57.36 | 6.02 | 11.15 |
| | | | | | | | | | | found | 57.06 | 5.95 | 11.10 |
| 24 | " | | " | —C$_2$H$_5$ | " | —C— ‖ O | " | 2HCl | 142–145 | calcd. | 56.42 | 6.19 | 10.12 |
| | | | | | | | | | | found | 56.10 | 5.99 | 10.06 |
| 25 | " | | " | n-C$_3$H$_7$ | " | O ‖ —C— | " | " | 133–137 | calcd. | 57.14 | 6.39 | 9.87 |
| | | | | | | | | | | found | 56.98 | 6.35 | 9.65 |

EXAMPLE 8

Acute toxicity

The present compound (Compound No. 12) was orally administered to mouse and the acute toxicity value (LD$_{50}$) was calculated according to Litchfield-Wilcoxon method.

LD$_{50}$ of this compound was more than 3000 mg/kg.

EXAMPLE 9

Hypotensive activity

As the experimental animal, spontaneous hypertensive rats 5 to 7 months after birth with a body weight of 300 to 370 g were used. The blood pressure and the heart beat of the non-narcotized, heart-cathetherized rats were operatively determined to calculate the averages in blood pressure and heart beat prior to the administration of the present compound. Successively during 6 hours after orally administering the present compound, the blood pressure and heart beat were determined to calculate the hypotensive ratio by the following formula:

$$\text{hypotensive ratio (\%)} = \frac{X - Y}{X} \times 100$$

wherein

X is the average in blood pressure before administration; and

Y is the value of the lowest blood pressure after the administration.

The results are shown in Table 2.

TABLE 2

| | dose (mg/kg) Hypotensive ratio (%) | | | | |
|---|---|---|---|---|---|
| Compound No. | 0.1 | 0.3 | 1 | 3 | 10 |
| 1 | 12.1 | 19.1 | 18.1 | 41.8 | — |
| 2 | 17.1 | 37.6 | 44.2 | — | — |
| 5 | 11.0 | 18.4 | 23.1 | — | — |
| 8 | 12.2 | 16.0 | 27.3 | — | — |
| 9 | 9.6 | 12.1 | — | — | 19.9 |
| 12 | 12.9 | 22.1 | 24.2 | 28.6 | — |
| 17 | — | 24.5 | 30.6 | 29.8 | — |
| Control | — | — | 18.2 | 20.8 | — |

Control: 3-[2-[4-(2-methoxyphenyl)-1-piperazinyl]ethyl]-1,2,3,4-tetrahydroquinazoline-2,4-dione

What is claimed is:

1. A phenylpiperazine compound having the formula:

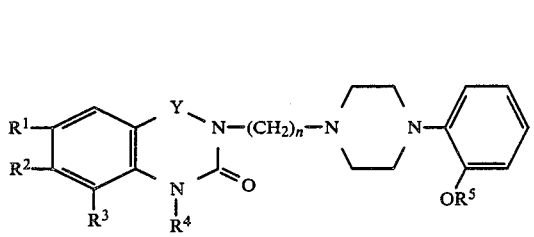

wherein $R^1$ and $R^2$ are each independently an alkoxy group of 1 to 3 carbon atoms, or $R^1$ and $R^2$ together with carbon atoms to which they are attached form —O(CH$_2$)$_m$O— wherein m is an integer of 1 to 3; $R^3$ and $R^4$ are each hydrogen; Y is —CO—; $R^5$ is hydrogen or an alkyl group of 1 to 3 carbon atoms; and n is an integer of 2 to 4; or an acid addition salt thereof.

2. The compound according to claim 1, wherein the alkoxy group is methoxy.

3. The compound according to claim 2, wherein alkoxy group is methoxy.

4. The compound according to claim 1, wherein the acid addition salt is dihydrochloride.

5. A phenylpiperazine compound having the formula:

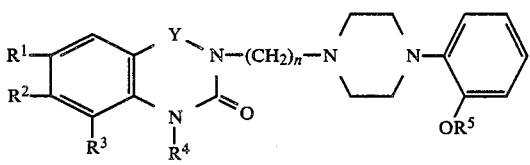

wherein
$R^1$, $R^2$ and $R^3$ are each independently hydrogen or an alkoxy group of 1 to 3 carbon atoms or
$R^1$ and $R^2$ or $R^2$ and $R^3$ together with carbon atoms to which they are attached form —O(CH$_2$)$_m$O— wherein m is an integer of 1 to 3, or
either $R^1$ or $R_2$ is an amine residue selected from the group consisting of —NH$_2$, —NHSO$_2$CH$_3$, —NHCOCH$_3$ and —NHCONH$_2$ and the other group is hydrogen or an alkoxy group of 1 to 3 carbon atoms and $R^3$ hydrogen;
$R^4$ is hydrogen and R5 is hydrogen or an alkyl group of 1 to 3 carbon atoms;
Y is —SO$_2$—; and
n is an integer of 2 to 4, or an acid addition salt thereof.

6. The compound according to claim 5, wherein the acid addition salt is the dihydrochloride salt.

7. A pharmaceutical composition for treating hypertension comprising an effective amount of a phenylpiperazine compound of the formula:

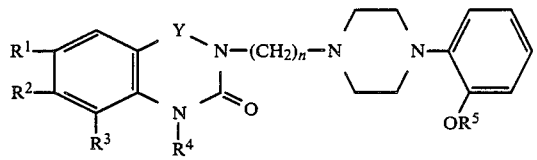

wherein $R^1$ and $R^2$ are each independently an alkoxy group of 1 to 3 carbon atoms, or $R^1$ and $R^2$ together with carbon atoms to which they are attached form —O(CH$_2$)$_m$O— wherein m is an integer of 1 to 3; $R^3$ and $R^4$ are each hydrogen; Y is —CO—; $R^5$ is hydrogen or an alkyl group of 1 to 3 carbon atoms; and n is an integer of 2 to 4; or an acid addition salt thereof.

8. The composition according to claim 7, wherein it is a solid or liquid dosage unit form intended for oral administration.

9. The composition according to claim 7, wherein it is a liquid dosage unit form intended for parenteral administration.

10. The composition according to claim 7, wherein said effective amouont is such that a daily dose of 0.1 to 100 mg per kg of body weight is provided.

11. The composition according to claim 8, wherein said liquid dosage formed comprises 0.5 to 10% by weight of the phenylpiperazine derivative.

12. The composition according to claim 8, wherein said solid dosage formed comprises 5 to 500 mg of the phenylpiperazine derivative.

13. A pharmaceutical composition for treating hypertension comprising an effective amount of a phenylpiperazine compound of the formula:

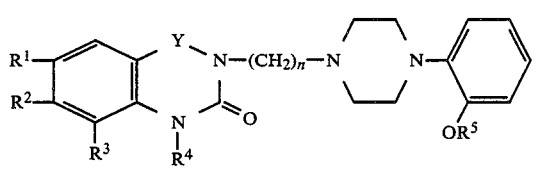

wherein
$R^1$, $R^2$ and $R^3$ are each independently hydrogen or an alkoxy group of 1 to 3 carbon atoms, or
$R^1$ and $R^2$ or $R^2$ and $R^3$ together with carbon atoms to which they are attached form —O(CH$_2$)$_m$O— wherein m is an integer of 1 to 3, or
either $R^1$ or $R^2$ is an amine residue selected from the group consisting of —NH$_2$, —NHSO$_2$CH$_3$, —NHCOCH$_3$ and —NHCONH$_2$ and the other group is hydrogenor an alkoxy group of 1 to 3 carbon atoms and $R^3$ is hydrogen;
$R^4$ is hydrogen and $R^5$ is hydrogen or an alkyl group of 1 to 3 carbon atoms;
Y is —SO$_2$—; and
n is an integer of 2 to 4, or an acid addition salt thereof.

14. The composition according to claim 13, wherein said effective amount is such that a daily dose of 0.1 to 100 mg/kg of body weight is provided.

15. The composition according to claim 13, wherein it is a solid or liquid dosage unit form intended for oral administration.

16. The composition according to claim 15, wherein said liquid dosage form comprises 0.5 to 10% by weight of the compound, and said solid dosage form comprises 5 to 500 mg of the compound.

* * * * *